(12) United States Patent
Sircar et al.

(10) Patent No.: US 6,927,047 B1
(45) Date of Patent: Aug. 9, 2005

(54) MANUFACTURE AND PURIFICATION OF MYCOPHENOLIC ACID

(75) Inventors: Anindya Sircar, Karnataka (IN); Shrikumar Suryanarayan, Karnataka (IN); Anand Prakash Khedkar, Karnataka (IN); Pampapathy Subramaniyam, Karnataka (IN); Shreehas Pradeep Tambe, Bangalore (IN)

(73) Assignee: Biocon Limited, Bangalore (IN)

( * ) Notice: Subject to any disclaimer, the term of this patent is extended or adjusted under 35 U.S.C. 154(b) by 0 days.

(21) Appl. No.: 10/220,225

(22) PCT Filed: Feb. 29, 2000

(86) PCT No.: PCT/IN00/00017

§ 371 (c)(1),
(2), (4) Date: Oct. 23, 2003

(87) PCT Pub. No.: WO01/64931

PCT Pub. Date: Sep. 7, 2001

(51) Int. Cl.$^7$ .............................................. C12P 17/04
(52) U.S. Cl. ...................................... 435/126; 435/123
(58) Field of Search ................................. 435/123, 126

(56) References Cited

U.S. PATENT DOCUMENTS 4,452,891 A     6/1984   Kida et al. .................. 435/126

FOREIGN PATENT DOCUMENTS

WO     WO00/29544     5/2000     ............ C12M 1/14
WO     WO 00/29544    5/2000

OTHER PUBLICATIONS

Abs JP359091891A Ozaki et al May 26, 1984.*
Muth, W.L. et al. "Biosynthesis of mycophenolic acid: purification and characterization of S-adenosyl-L-methionine: demethylmycophenolic acid O-methyltransferase." Antimicrob. Agents and Chemother. (1975), 8(3), pp. 321-327 (abstract only).
Sudhukhan, A.K. et al. "Optimization of mycophenolic acid production in solid state fermentation using rsponse surface methodology." Journal of Industrial Microbiology & Biotechnology (1999) 22, pp. 33-38.
B. Gosivo, Riv. Igiene Sanita Pub. Ann, 7, 825-869, 1896.
Muth and Nash, Antimicrobial Agents and Chemotherapy, 8, 321-327, 1896.
Sadhukhan et al. J. Ind. Microbiol, Biotechnol.22, 33-38, 1999.

* cited by examiner

Primary Examiner—Herbert J. Lilling
(74) Attorney, Agent, or Firm—Sidley Austin Brown & Wood LLP

(57) ABSTRACT

The present invention provides an improved method for the manufacture of Mycophenolic acid by solid substrate fermentation of *Pencillium brevi-campactum*, in a contained bioreactor under optimal fermentation parameters with its subsequent purification steps.

10 Claims, No Drawings

MANUFACTURE AND PURIFICATION OF MYCOPHENOLIC ACID

FIELD OF THE INVENTION

The present invention relates to an improved method for the manufacture and purification of Mycophenolic acid (MPA).

BACKGROUND OF THE INVENTION

Mycophenolic acid (MPA) was initially isolated from a culture of *Penicillium* (B. Gosio, Riv. Igiene Sanita Pub. Ann, 7, 825–869, 1896). Its value as an immunomodulator was realized much later. Morpholino ester of mycophenolic acid is used as a prodrug in pharmaceutical composition for treatment of rheumatoid arthritis, psoriasis and in prevention of tissue rejection in organ transplant patients.

Mycophenolic acid is produced by aerobic fermentation of several *Penicillium* species. It has a broad spectrum of activity like antitumor activity, antiviral, antipsoriatic, immunosuppressive and anti-inflammatory activity. It also exhibits antibacterial and antifungal activities. It is tolerable in large doses and has minimal side effects. It inhibits inosine monophosphate dehydrogenase which is an important enzyme in de novo synthesis of inosine monophosphate, a precursor of purines. MPA also inhibits proliferation of lymphocytes that are responsible for immune response. This immuno repressory effect of mycophenolic acid has been important in treatment of organ rejection after organ transplant surgery.

There is a continuous need to find improved process for production of mycophenolic acid that will be commercially viable. It has been shown that mutants *Penicillium brevi-compactum* resistant to polyene antibiotics, HMG CoA reductase inhibitors, methyl viologen and surfactants produce more MPA than the parent strain (U.S. Pat. No. 4,452,891).

The proposed biosynthetic pathway of mycophenolic acid production involves steroid biosynthetic pathway as well as polyketide biosynthetic pathway. It is a condensation product of a tetraketide and geranyl pyrophosphate, wherein geranyl moiety is cleaved after condensation and subsequent o-methylation in the tetraketide ring yields mycophenolic acid (Muth and Nash, Antimicrobial Agents and Chemotherapy, 8, 321–327, 1896). The biosynthetic pathway was studied in *P. stoloniferum*.

*Penicillium brevi-compactum* strain has been used in submerged fermentation where it produces 2.4 mg/ml at 27° C. in 6 days on shaking and gives 3.6 mg/ml at 27° C. in 14 days without shaking (U.S. Pat. No. 4,452,891). In solid substrate fermentation (SSF) it is reported to produce 3286 mg per Kg of wheat bran (Sadhukhan et al, J. Ind. Microbiol. Biotechnol. 22, 33–38, (1999). Regarding the economics of using a producing strain, the described volume-time-yields as an industrial process are not economically attractive.

The object of the present invention is to provide an improved method for the production of mycophenolic acid by solid substrate fermentation in a novel bioreactor 'PLAFRACTOR' and its subsequent purification.

To achieve the said objective this invention provides an improved method for the manufacture of Mycophenolic acid comprising:
  loading a contained bioreactor with solid substrate matrix and sterilizing it,
  mixing the said sterilized solid substrate matrix with *Penicillium brevi-compactum*,
  adding 5–20% of glycerol, if desired,
  incubating the said inoculated solid substrate matrix for 4–7 days at 20–35° C.,
  extracting the fermented solid substrate matrix with an organic solvent,
  concentrating the organic solvent extract,
  crystallizing mycophenolic acid by adjusting the pH to about 2.0 with an inorganic acid and allowing to stand for about 3 hours, followed by filtration using a filter aid,
  dissolving the filter aid cake in a water immiscible organic solvent and treating with alumina,
  filtering the water immiscible organic solvent followed by concentration of the organic layer by distillation,
  dissolving the concentrate obtained in an alcohol,
  dispersing the alcoholic solution in water and filtering to get the crude crystals,
  dissolving the crude crystals thus obtained in an organic solvent,
  adding another organic solvent to the previous step solution and chilling to 4 to −20° C. to get pure mycophenolic acid crystals.

The *Penicillium brevi-compactum* used is in the form of spore suspension or in mycelial form.

The solid substrate matrix is selected from wheat bran, rice bran, ragi flour, soya flour, cotton seed flour, wheat flour, rice flour, rice husk.

The solid substrate matrix is a mixture of two or more solid substances selected from wheat bran, rice bran, ragi flour, soya flour, cotton seed flour, wheat flour, rice flour, rice husk.

The said contained bioreactor allows solid state fermentation to be carried out in a manner such that the fermentation micro-organisms and the fermentation products produced are kept isolated from the outside environment during the course of fermentation. The said contained bioreactor is "PLAFRACTOR".

The organic solvent used for extraction is selected from acetone, ethanol, toluene, benzene or ethyl acetate.

The filter aid is selected from celite, perlite or alumina.

The solvent used to dissolve the filter aid cake is selected from cyclohexane, toluene, benzene, ethyl acetate or butyl acetate.

The alcohol used for crystallization is selected from methanol, ethanol or iso-propanol.

The inorganic acid used for adjusting pH is sulphuric acid and the concentration of the organic layer is carried out by azeotropic distillation.

The present invention uses *Penicillium brevi-compactum*. The colony of this isolate was comparatively fast growing and the aerial mycelium was cottony and white. The microbial culture sporulated showing green coloration on third day.

The bioreactor used for the solid substrate fermentation is our invention and is described in our PCT publication no. WO 00/29544. The said bioreactor is modular in nature and carries out all of the processes of solid substrate fermentation in a single contained environment. The modular construction of the bioreactor provides multiple modules stacked on top of one another, each with a base connected to frame for holding the solid medium in isolation from the exterior environment. The construction of the bioreactor allows solid substrate fermentation to be carried out in a manner such that the fermenting microorganisms and the fermentation products it produces are kept isolated from the outside environment during the course of the fermentation. This containment of the fermentation process is of significant importance when working with microbial metabolites, which are cytotoxic in nature e.g. Cyclosporin, mycophenolic acid.

The said bioreactor operates in a contained manner and is capable of sterilizing the solid state fermentation media, cooling it to the required temperature, fermenting at the desired set conditions, in situ extraction of the end product, recovery of the solvents and post harvest sterilization.

An important aspect of the bioreactor is a mechanism of heat removal resulting in stringent temperature control of the fermentation process. In comparison, maintaining a constant temperature of growth in solid substrate fermentation using tray cultures is not efficient. The base plate of the bioreactor has multiple channels called noncommunicating channels that carry heating and cooling fluids sandwiched between two sheets. Heat is transferred to and from the modules by conduction. In this way the temperature of the module is precisely maintained to meet the specific requirement of different microorganisms.

The base of the module contains a second set of channels, the communicating channels to deliver sterile air as supply of oxygen into the solid substrate bed for optimum growth of organism. Moisture loss because of passage of sterile air is significantly reduced by regularly reversing the direction of airflow every few hours. Using this, homogeneity in moisture content is maintained throughout the bioreactor. These aspects provide ample convenience over previous SSF methodologies that require multiple manipulations at each step of the fermentation process.

The invention will now be described with reference to the following examples:

EXAMPLE 1

A single spore isolate of *Penicillium brevi-compactum* was used. The organism was subcultured on a fresh MEA (Malt Extract Agar) slant and incubated at 24° C. After 5 days, the sporulated slant was suspended in 10 ml of water containing 0.01% tween 80. 500 µl of this spore suspension were spread on a fresh plate containing MEA. The plate was allowed to grow for 5 days. After 5 days the spores were scraped from the plate with a sterile loop and suspended in sterile distilled water. This spore suspension, devoid of mycelial fragments was used as the inoculum. 15 Kg of wheat bran was loaded on the bioreactor of approximately 22600 $cm^2$ of plate area. The bioreactor was sterilized by sending steam simultaneously into the communicating and the noncommunicating channels to heat the bioreactor and its contents to a temperature of 121° C. for 90 minutes. The steam pressure was released and simultaneously sterile air was sent into the communicating channels while cooling water at approximately 25° C. was sent into the noncommunicating channels.

The master seed for inoculation of culture was a $10^6$ spores/ml suspension of *Penicillium brevi-compactum* in 14 L of sterilized distilled water containing 20% glycerol. This was used to inoculate the sterilized wheat bran so that the final moisture after inoculation was 60%. The inoculum was mixed thoroughly with the sterilized bran. Sterile airflow at a rate of 20 Lpm on the first day, 40 Lpm on second and third day and 20 Lpm on fourth and fifth day were sent into the bioreactor continuously. The temperature was controlled at 25° C. for all 5 days by conductive heating and cooling. The Mycophenolic acid production titres were assayed following extraction using the HPLC.

EXAMPLE 2

The Bioreactor was sterilized and inoculated as in Example 1. In this experiment, the temperature was maintained at 30° C. for all 5 days. The Mycophenolic acid production titres were assayed following extraction using the HPLC.

EXAMPLE 3

5 Kg. fermented wheat bran obtained from example 1 was then extracted by using 10 L of acetone and the extract was collected, analyzed and taken for further processing. The extraction efficiency of acetone was found to be 98%, as quantitated by HPLC.

EXAMPLE 4

The extract obtained from Example 3 was concentrated by azeotropic distillation to remove acetone, leaving behind 1.5 L of aqueous residue. The pH of this aqueous residue was adjusted to 2.0 with concentrated $H_2SO_4$ and allowed to stand at 10° C. After 4 hours large needle shaped crystals of Mycophenolic acid were found floating at the surface of the liquid. These crystals were separated by filtration through a celite bed. Recovery of mycophenolic acid by this crystallization was found to be 100%. Crystals trapped on the celite bed were re-dissolved completely in 2 L of ethyl acetate. Ethyl acetate layer was separated and treated with alumina to remove colour. Alumina was removed by filtration and ethyl acetate layer was concentrated by distillation to leave behind light brown coloured crystals of mycophenolic acid. These crystals were further dissolved in methanol and dispersing the methanolic solution in water to obtain white crystals of mycophenolic acid. These crystals obtained from aqueous methanol were dissolved in 10 parts of acetone. To this acetone solution equivalent amount of hexane was added and the mixture was chilled to 10° C. The crystals of mycophenolic acid were separated by filtration and dried. The crystals thus obtained were of acceptable pharmaceutical grade.

The present invention has the following advantages over the other reported methods:

(i) Fermentation in a bioreactor, which is fully contained as a result assuring full safety for the cytotoxic fermentation products like mycophenolic acid.
(ii) In situ extraction of the fermented end product.
(iii) Less fermentation time making the process economically attractive.
(iv) Fewer steps for the isolation and purification to get the pure product, thus saving processing time and additional expenses.

What is claimed is:

1. A method for the manufacture of Mycophenolic acid comprising:
    loading a contained bioreactor with solid substrate matrix and sterilizing it,
    mixing the said sterilized solid substrate matrix with *Penicillium brevi-compactum*,
    adding 5–20% of glycerol, if desired,
    incubating the said inoculated solid substrate matrix for 4–7 days at 20–35° C.,
    extracting the fermented solid substrate matrix with an organic solvent, concentrating the organic solvent extract, crystallizing mycophenolic acid by adjusting the pH to 2.0 to 5.0 with an inorganic acid and allowing to stand for 3 to 10 hours, followed by filtration using a filter aid, dissolving the filter aid cake in a water immiscible organic solvent and treating with alumina, filtering the water immiscible organic solvent followed by concentration of the organic layer by distillation, dissolving the concentrate obtained in an alcohol, dispersing the alcoholic solution in water and filtering to get the crude crystals, dissolving the crude crystals thus obtained in an organic solvent, adding another organic solvent to the previous step solution and chilling to 4 to −20° C. to get pure mycophenolic acid crystals.

2. A method as claimed in claim 1 wherein *Penicillium brevi-compactum* used is in the form of spore suspension or in mycelial form.

3. A method as claimed in claim 1 wherein the solid substrate matrix is selected from wheat bran, rice bran, ragi flour, soya flour, cotton seed flour, wheat flour, rice flour, nice husk.

4. A method as claimed in claim 1 wherein the solid substrate matrix is a mixture of two or more solid substances selected from wheat bran, rice bran, ragi flour, soya flour, cotton seed flour, wheat flour, rice flour, rice husk.

5. A method as claimed in claim 1 wherein the organic solvent used for extraction is selected from acetone, methanol, toluene, benzene or ethyl acetate.

6. A method as claimed in claim 1 wherein the filter aid is selected from celite, perlite or alumina.

7. A method as claimed in claim 1 wherein the solvent used to dissolve the filter aid cake is selected from cyclohexane, toluene, benzene, ethyl acetate or butyl acetate.

8. A method as claimed in claim 1 wherein the alcohol used for crystallization is selected from methanol, ethanol or iso-propanol.

9. A method as claimed in claim 1 wherein the inorganic acid used for adjusting pH is sulphuric acid.

10. A method as claimed in claim 1 wherein the concentration of the organic layer is carried out by azeotropic distillation.

* * * * *